US00PP11429P

United States Patent [19]

Verwer

[11] Patent Number: Plant 11,429

[45] Date of Patent: Jun. 27, 2000

[54] DAHLIA PLANT NAMED 'KARMA SERENA'

[75] Inventor: Aad Verwer, Lisse, Netherlands

[73] Assignee: Fa. Gebr. Verwer, Lisse, Netherlands

[21] Appl. No.: 09/026,003

[22] Filed: Feb. 19, 1998

[51] Int. Cl.[7] ..... A01H 5/00

[52] U.S. Cl. ..... Plt./321

[58] Field of Search ..... Plt./321

[56] References Cited

U.S. PATENT DOCUMENTS

P.P. 1,386 4/1955 Curtis et al. ..... Plt./321

OTHER PUBLICATIONS

GTITM UPOVROM Citation for 'Karma Serena' as per NL PBR DHL0067; Feb. 16, 1996.

GTITM UPOVROM Citation for 'Karma Serena' as per QZ PBR 970258; Feb. 17, 1997.

GTITM UPOVROM Citation for 'Karma Serena' as per GB BIL 09900071.

*Primary Examiner*—Howard J. Locker

*Assistant Examiner*—Kent L. Bell

*Attorney, Agent, or Firm*—Christie, Parker & Hale, LLP

[57] ABSTRACT

A dahlia plant variety producing white flowers with yellow center.

1 Drawing Sheet

BACKGROUND OF THE INVENTION

The present invention relates to a new and distinct variety of *Dahlia hybrida* known by the varietal denomination 'Karma Serena'. The female parent of 'Karma Serena' is a variety known as 'Ambiance' and the male parent is the variety known as 'Oriental Dream', both of which are not known to be patented.

SUMMARY OF THE INVENTION

The new variety is a dahlia plant useful for growing outdoors and under glass which produces attractive creamy white flowers with yellow-green centers on long stems. Among the traits possessed by the new variety which in combination distinguish it from other varieties known to the inventor are its attractive flowers borne on long stems.

Asexual reproduction by cuttings of the new variety in The Netherlands has demonstrated that the combination of characteristics as described herein for 'Karma Serena' are firmly fixed and are retained through successive generations of asexual reproduction.

COMPARISON WITH PARENTS

The new variety differs from its parents in flower color.

BRIEF DESCRIPTION OF ILLUSTRATION

The accompanying color photographic illustration shows a typical bloom and leaves of the new variety in colors as nearly true as possible with an illustration of this type.

DESCRIPTION OF THE NEW VARIETY

In the following description, color references are to The Royal Horticultural Society Colour Chart, where color values refer to color plate numbers in this chart.

The following observations are of plants described and grown in The Netherlands under outdoor conditions which approximate those generally used in commercial practice.

'Karma Serena' has not been observed under all possible environmental conditions. The phenotype may vary with variations in environment such as temperature, light intensity, day length and cultural conditions.

Parentage:

*Female parent.*—'Ambiance'.

*Male parent.*—'Oriental Dream'.

Plant:

*Form.*—Upright, spreading, bushy.

*Height.*—About 80 cm.

*Branching characteristics.*—Freely branching.

*Natural flowering season.*—July to November in The Netherlands under glass.

*Hardiness.*—Plants are winter hardy to 0° C.

*Disease resistance.*—Similar to the species.

*Flower stem.*—Length: About 60 cm. Color: Near 151A.

*Foliage.*—Quantity: Many. Leaf arrangement: Opposite, single or compound; compound leaves of either 3 or 5 leaflets; single leaf size about 8.9 cm long, about 5.3 cm wide; compound leaf size about 26 cm long, about 16 cm wide; apex is acute, base is acute. Shape of leaf: Ovate. Leaf edge: Dentate. Texture: Leaf upperside: Smooth. Leaf under side: Smooth. Color: Leaf upperside: Near 146A. Leaf under side: Near 147C. Venation: Pinnate. Petiole length: Terminal, about 15 cm, lateral about 5 cm. Stipules: None. Stem color: Near 151A.

*Sepals.*—Number: About 35. Length: About 2.1 cm. Width: About 1.5 cm. Color: Near 137A. Base: Rounded. Apex: Broadly acute.

Bud:

*Form.*—Globular.

*Size.*—About 1 cm.

*Opening rate.*—About 14 days.

*Color of ray florets.*—When sepals first divide near 155A; when ray florets begin to unfurl near 155A.

Flower:

*Inflorescence form.*—Blooms borne singly.

*Bloom form.*—Decorative.

*Bloom diameter.*—About 12 cm.

*Flowering.*—About 2 to 3 main branches are produced, with flowering occurring 30 to 35 days later.

*Color tonality from a distance.*—Creamy white.

*Lasting quality.*—About 20 to 25 days on plant; 10 to 12 days after cutting.

*Ray florets.*—Length: About 6.1 cm. Width: About 2.3 cm. Shape: Oblong. Apex: Obtuse. Base: Rounded.

*Color.*—Creamy white with yellow at center. Inner ray florets (upper surface and undersurface): Near 155A. Outer ray florets (upper surface and undersurface) attachment: Near 1B. As bloom ages: Flowers keep color. Fragrance: None.

*Disc florets.*—Number: About 30. Length: About 1.3 cm. Color: Near 7A. Shape: Cylindric.

Reproductive organs:

*Stamens.*—Tubular, pointed near 17A

*Anthers.*—Small, near 17A. .

*Pollen.*—Near 17A.

*Pistils.*—Styles near 9B; stigmas divided, near 9B.

*Character of ovaries.*—1 per pistil.

I claim:

1. A new and distinct dahlia plant of the variety substantially as shown and described.

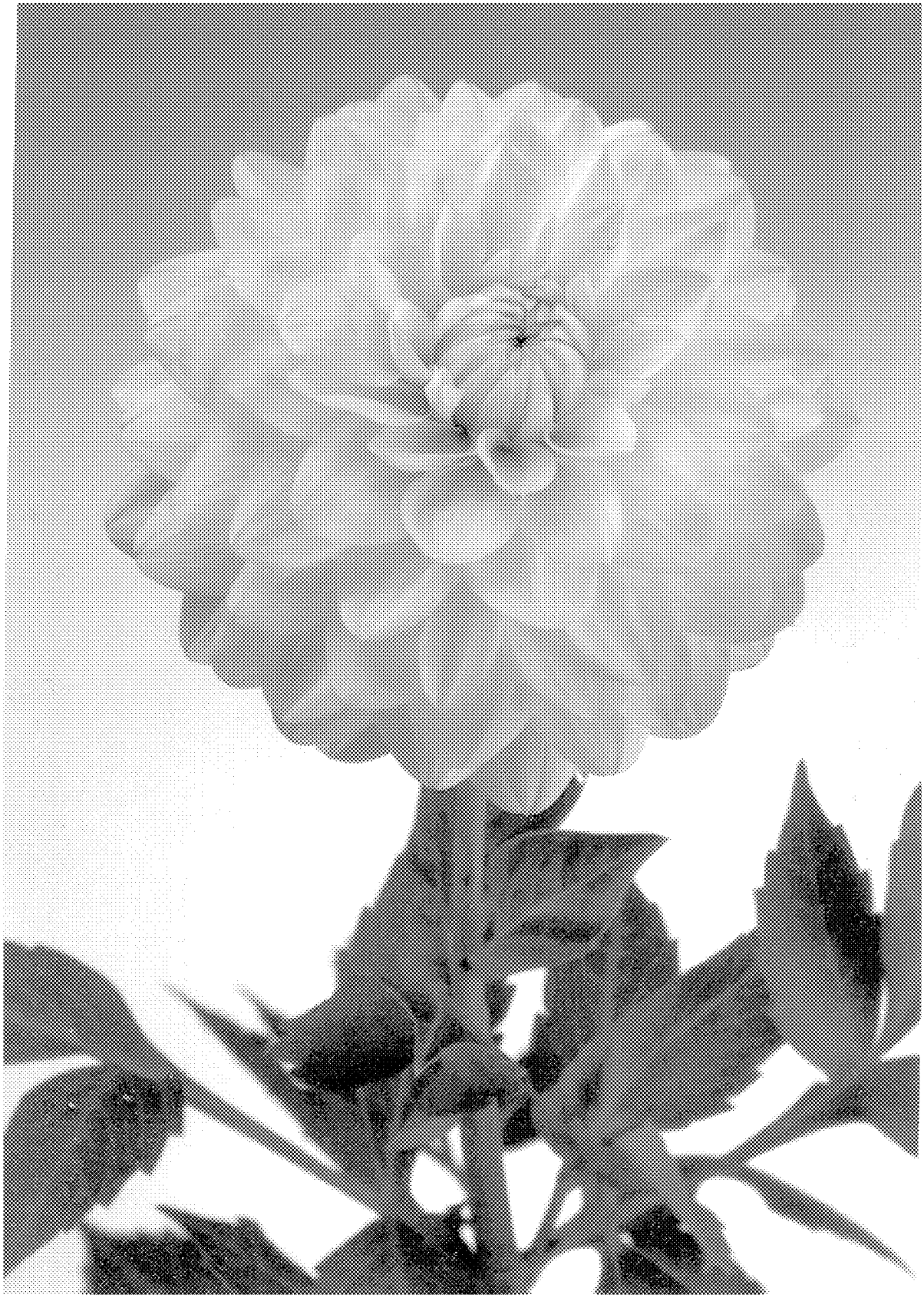

* * * * *